US006372718B2

(12) United States Patent
Santar et al.

(10) Patent No.: US 6,372,718 B2
(45) Date of Patent: *Apr. 16, 2002

(54) COMPOSITION CONTAINING STABLE MICRODISPERSED POLYANHYDROGLUCURONIC ACIDS AND SALTS THEREOF

(75) Inventors: Ivan Santar, Predklasteri; Frantisek Kiss, Brno; Jiri Briestensky, Cernilov, all of (CZ)

(73) Assignee: Alpenstock Holdings Limited, Sallynoggin (IE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/359,588

(22) Filed: Jul. 26, 1999

Related U.S. Application Data

(63) Continuation of application No. PCT/IE98/00004, filed on Jan. 30, 1998.

(30) Foreign Application Priority Data

Jan. 30, 1997 (IR) .................................................. 970061

(51) Int. Cl.$^7$ ........................ A01N 43/04; S61K 31/70; S61L 9/04
(52) U.S. Cl. ............................ 514/25; 514/54; 424/45; 424/489
(58) Field of Search ....................... 514/25, 54; 424/45, 424/489

(56) References Cited

U.S. PATENT DOCUMENTS

| 3,364,200 A | 1/1968 | Ashton et al. ............... 260/212 |
| 4,100,341 A | 7/1978 | Brasey ......................... 536/56 |
| 4,347,057 A | 8/1982 | Yasnitsky et al. .............. 8/116 |

FOREIGN PATENT DOCUMENTS

| CZ | 185366 | 1/1978 |
| DE | 941289 | 4/1956 |
| DE | 967144 | 10/1957 |
| EP | 0492990 | 9/1995 |
| GB | 709684 | 6/1954 |
| GB | 1049636 | 11/1966 |
| GB | 1593513 | 7/1981 |
| SU | 937462 | 12/1980 |

OTHER PUBLICATIONS

Kenyon et al, Industrial and Engineering Chemistry, "Oxidation Of Cellulose", pp. 2–9, Jan. 1949.
F. Alhaique et al, Farmaceutica, "Oxidized scleroglucan for the design of pH", pp. 11–15, 1986.
E.P. Kaversneva, An SSSR, vol. 78(3), pp. 481–483, 1951.
Pasteka M. Chemicke Zvesti (Slovakia), 20, pp. 855–861, 1966.
J. Briestensky et al., Chemical Abstracts, vol. 110, No. 14, "Production of oxidized cellulose–based sorbent as a resorable hemostatic material", 1 page, Apr. 3, 1989.
T. Painter, Carbohydrate Research, vol. 140, "New Gucuronoglucans Obtained By Oxidation Of Amylose At Position 6", pp. 61–68, 1985.
T.P. Nevell, The Journal of the Textile Institute, "The Oxidation Of Cotton Cellulose By Nitrogen Dioxide", pgs. T91–T129, Mar. 1951.
H. Sihtola et al., Journal of Polymer Science: Part C, No. 2, "Classification of Carbonyl Groups in Cellulose on the Basis of their Reaction Rates at Oximation", pgs. 289–309, 1963.
S. W. Chaikin et al., Journal of Am. Chemical Society, vol. 71, Reduction of Aldehydes, Ketones and Acid Chlorides by Sodium Borohydride, pgs. 122–125, Jan. 1949.

*Primary Examiner*—Raj Bawa
(74) *Attorney, Agent, or Firm*—Jacobson Holman, PLLC

(57) ABSTRACT

Stable microdispersed polyanhydroglucuronic acid and salts thereof contain in their polymeric chain from 8 to 30 per cent by weight of carboxyl groups, at least 80 per cent by weight of these groups being of the uronic type, at most 5 per cent by weight of carbonyl groups including intra- and intermolecular 2,6 and 3,6 hemiacetals, 2,4-hemialdals and C2–C3 aldehydes. The molecular mass of the polymeric chain is from $1 \times 10^3$ to $3 \times 10^5$ Daltons. The microdispersed products are prepared by subjecting a polyanhydroglucuronic acid-containing material to partial or complete hydrolysis and neutralisation in an oxidative environment.

11 Claims, No Drawings

COMPOSITION CONTAINING STABLE MICRODISPERSED POLYANHYDROGLUCURONIC ACIDS AND SALTS THEREOF

This application is a continuation of PCT/IE98/00004, filed Jan. 30, 1998.

The present invention relates to a stable microdispersed polyanhydroglucuronic acid (PAGA) and salts thereof, especially suitable for medicinal, pharmaceutical and cosmetic products, as well as to a method of preparing the same. The term polyanhydroglucuronic acid and salts thereof as used herein includes copolymers thereof, especially with anhydroglucose.

INTRODUCTION

Besides proteins, polysaccharides represent the most widespread biopolymers found in the biosphere. As an example, up to $10^{12}$ metric tonnes per year of cellulose, a 1, 4 βD-glucane, is synthesized in nature. Other α and β glucanes bound e.g. by 1,2; 1,3; 1,4 and 1,6; or 1,2 and 1,4 glycosidic bonds in the main chain, mostly of microbial origin, gain increasing importance with ongoing research in the field. It is the presence of glucuronic acid units in the polymeric chain of the oligosaccharides or polysaccharides that, together with their molar mass and type of the principal glycosidic bond, constitutes the basis of their immunostimulative, antitumourous, anticoagulative, or else haemostyptic effects (cf. Burchard. W. Ed., Polysaccharide, Eigenschaften and Nutzung, Springer Verlag, Berlin 1985, p. 144).

Glucuronoglucanes can preferably be prepared by relatively specific selective oxidation of the primary alcoholic group at C6 carbon atom of the glucopyranosic unit of natural polysaccharides by nitrogen oxides, the C1 aldehydic group of the basic unit being protected by the glycosidic bond.

A variety of methods have been disclosed for preparing glucuronoglucanes and glucuronanes from natural glucanes, using the oxidative effects of $NO_x$ either in the gaseous form (Kenyon et al., Ind. Eng. Chem., 41, No 1, 2–8 (1949); DE 0941289; DE 0967144), in nonpolar reaction environment of inert liquids such as hydrogenated hydrocarbons (USSR SU 937462; U.S. Pat. No. 4,347,057; EP 0492990), or in polar environment of aqueous solutions of acids such as $HNO_3$, $H_3PO_4$ or their mixtures with $HSO_4$, wherein the $NO_x$ are mostly generated directly the oxidation liquor via dosed introduction of reducing substances such as, notably, $NaNO_2$ (GB 709684; CS AO 185366; GB 1593513; Painter J. et al., Carbohydrate Research 140, 61 (1985); Alhaique F., Chim. Oggi 11–15, 17 (1986)), or the reaction environment is created by introducing liquid $NO_x$ into aqueous $HNO_3$ (U.S. Pat. No. 4,100,341).

A disadvantage of these known processes relates to the fact that their oxidative effects on the glucane molecule are non-uniform and only relatively specific in that besides creation of carboxyl groups of the uronic type of C6 carbon of the glucopyranosic unit, other types of successive reactions (such as formation of $ONO_2$ and NO groups on C6) and secondary reaction (such as formation of COOH and other oxidised groups on end carbons C1 and C4, and notably on C2 and C3 carbons) do occur. In accord with numerous publications (Kaversneva E. P., Doklady AN SSSR (U.S.S.R.) 78 (3), 481 (1951); Nevell T. P., J. Text. Ind. 42, 91 (1951); Sihtola M. et al., J. Polym. Sci, Part C, (2), 289 (1963); Pastéka M., Chemické Zvesti (Slovakia) (20), 855 (1966)), extensive testing of polyanhydroglucuronic acids prepared by the action of $NO_x$ has led us to the conclusion that, besides carboxyl groups on C6 carbon, several other aldehydes, ketones, and their condensation products are formed that have fundamental influence on the stability of the polyanhydroglucuronic acid product.

It is known that the presence of carbonyl groups can be limited by their back reduction to primary alcoholic groups by means of complex hydrides such as $NaBH_4$ (Charkin S. W. and Brown W. G., J. Am. Chem. Soc. 71, 122 (1949); Mead F. S. M., J. Text, Inst. 46, T 400 (1955)), but this process is quite expensive for industrial use due to the cost of the hydrides.

The quality of the product also depends on both the input raw material and the technological method used. Natural glucanes occur in the form of fibres, globules or grains with varying degree of orderliness (crystallinity). Their oxidation and partial degradation due to the effect of $NO_x$ does not proceed with the same speed in crystalline and amorphous regions, so that the resulting product represents a mixture of macromolecules oxidised and degraded to various extents which may provide products which are physiologically ineffective and/or have negative effects.

It is evident from the above that the preparation of stable PAGA product having required physical and chemical characteristics, destined for pharmaceutical and cosmetic use, is in no way a simple matter.

In health care practice one often encounters cases of capillary bleeding occurring during injuries or related to surgical interventions. The healing of the wounds frequently depends on attaining rapid homeostasis and creation of coagulum, to especially serve as a protection of the wound against infection. Application of D glucurono-1, 4 βD-glucane, the so-called oxidised cellulose, as a non-toxic resorbable local haemostatics to arrest bleeding from surface injuries or parenchymatous organs, osseous bleeding, and in general wherever use of conventional styptic means may be difficult or slow in functioning and less effective, has proved especially effective in similar cases.

Experience has shown that the product should be stored at temperatures not exceeding 25° C., preferably below 10° C., protected against direct light. When these conditions are not met, the influence of light and/or elevated temperatures during storage may easily provoke degradation changes due to the instability of secondary reactive groups and, on nitrogen-containing sites. This in turn may be manifested by reduced tissue tolerability, and even virtually exclude application of the conventional product in some pharmaceutical or cosmetic preparations.

In summary, methods of preparing PAGA known thus far are based on oxidative action of $NO_x$ on suitable types of polysaccharides of cellulosic or microbial origin (such as scleroglucanes), possibly with subsequent reduction of the content of destabilizing groups via reduction by hydrides, the latter process being, however, relatively expensive and jeopardising the product with simultaneous reduction of the carboxyl group content via reduction of their carbonyls. No method has been found up to now for preparing stable polyanhydroglucuronic acid with broader application scope enabling a better control of the final product characteristics.

Among important disadvantages of the known methods quoted above are non-uniform degree of both oxidation and degradation of individual polysaccharide particles or fibres, non-uniform content of bound nitrogen and other destabilizing sites in the macromolecule, as well as broad distribution of their molecular masses, altogether factors which can result in non-uniformity in resorbtion in the organism on applying the product as a haemostatic or in binding other substances or drugs such as anaesthetics, antibiotics or cytostatics.

In the latter case of active substance-PAGA complexes, the presence of destabilizing groups in this otherwise important biologically degradable carrier brings about inherent instability and changes in properties with time. The same applies to formulations for pharmaceutical or cosmetic use, for which our testing has revealed discoloration with temperature and time, viscosity changes, and even phase separation, whenever unstabilized PAGA prepared by known methods was utilised.

A further deficiency of the known methods lies in the fact that PAGA prepared by $NO_x$ oxidation displays closed surface and low values of specific surface area (measured $m^2.g^{-1}$) for both fibrillar or particulate material. Whenever final product in powder form is required, the isolated bulk product has to be mechanically disintegrated, in a dry or wet process, which brings about potential contamination by impurities such as metals due to abrasion of production equipment and increases further the production costs.

A last but not least disadvantage of the conventionally prepared PAGA products is that, in contrast to e.g. hyaluronic or algic acids, they do not allow conversion to a range of forms for different applications.

Some of the above deficiencies had been addressed by J Briestensky et al. (CS AAO 242920) who disclose an oxidised cellulose-based sorbent consisting of highly porous non-agglomerated particles of PAGA, and a method of manufacturing the same, involving transformation of oxidised cellulose into a colloidally dispersed system with simultaneous partial hydrolysis followed by coagulation and stabilisation.

However, the above issues relating to the inherent structural non-uniformity of the raw oxidised products and its long-term destabilising effects remain to be unsolved.

There is therefore a need for a method of preparing stable microdispersed polyanhydroglucuronic acid and salts thereof so that the product may be used in medicinal, pharmaceutical and cosmetic formulations.

BRIEF SUMMARY OF THE INVENTION

According to the invention there is provided a method for preparing a product comprising polyanhydroglucuronic acid and/or salts thereof wherein a polyanhydroglucuronic acid-containing material obtained by oxidation with nitrogen oxides is subjected to partial or complete hydrolysis and neutralisation in an aqueous solution of inorganic and/or organic salts and/or bases in the presence of suitable oxidising agents, the hydrolysate undergoing fractional coagulation to form a stable microdispersed/microdispersable product. The term polyanhydroglucuronic acid and salts thereof includes copolymers thereof, especially with anhydroglucose.

This method provides stable polyanhydroglucuronic acid and salts thereof in essentially a single process carried out in a single vessel.

Most preferably the inorganic and/or organic salts and/or bases used for hydrolysis are chlorides, sulphates, carbonates, formates, or acetates of alkali and/or alkaline earth metals, hydroxides of alkali and/or alkaline earth metals, alkylamines, or alkanolamines, in concentrations ranging from 1 to $10^{-3}$ to 5 mol/l.

In an especially preferred embodiment of the invention the oxidative environment during hydrolysis is established by the presence of oxidising agents selected from one or more of hydrogen, sodium or magnesium peroxide, peroxoacids and their salts, hypochlorites and chlorites.

Preferably the hydrolysate is let to undergo fractional coagulation by a suitable water-miscible organic solvent, the coagulated product is washed, or dehydrated, using a suitable water-miscible organic solvent, and/or converted, in an appropriate manner, for intended subsequent use.

Preferably the procedure is carried out at a pH of from 1 to 12, and preferably, at a temperature of from 0 to 100° C.

In a preferred embodiment of the invention the polyanhydroglucuronic acid-containing material is obtained by oxidation of a suitable polysaccharide, such as native or regenerated cellulose or starch.

The invention also provides stable microdispersed/microdispersable polyanhydroglucuronic acid and salts thereof wherever made using the method of the invention. In particular, the invention also provides novel stable microdispersed polyanhydroglucuronic acid and salts thereof containing in their polymeric chain from 8 to 30 per cent by weight of carboxyl groups, at least 80 per cent by weight of these groups being of the uronic type, at most 5 per cent by weight of carbonyl groups, and at most 0.5 per cent by weight of bound nitrogen.

Preferably the product contains at most 0.2 per cent by weight of bound nitrogen in the polymeric chain.

In a preferred embodiment of the invention the molecular mass of the polymeric chain is from $1 \times 10^3$ to $3 \times 10^5$ Daltons, most preferably from $5 \times 10^3$ to $1.5 \times 10^5$ Daltons.

The content of the carboxyl groups is in the range of from 12 to 26 per cent by weight and at least 95 per cent of these groups are of the uronic type.

In a particularly preferred embodiment of the invention the product contains at most 1 per cent by weight of carbonyl groups. Typically the carbonyl groups are intra- and intermolecular 2,6 and 3,6 hemiacetals, 2,4-hemialdals and C2–C3 aldehydes.

The polyanhydroglucuronic acid and salts thereof may be made up of particles sized from 0.1 to 100 $\mu$m and/or fibres of from 5 to 30 $\mu$m diameter and up to 30 mm length.

Because neutralisation and refining is carried out in a single operation the process is cost effective.

As the product is in a microdispersed form there is enhanced sorption and greater accessibility for blood. Therefore the biological availability is increased and a rapid onset of haemostasis. We have also observed that the product assists wound healing as a large surface area is presented which is quickly penetrated by body fluids and goes into solution in these fluids. We believe that the product then chemically degrades to achieve more rapid absorption and enhancement of the wound healing process.

The overall homogeneity of the distribution of oxidised groups within the product is increased. Thus, the product has improved reactivity and accessibility to reactive sites for the purpose of binding other substances such as pharmacologically active substances to the product. The average degree of polymerisation is decreased, the distribution of the polymerisation is narrowed and the amount of cellulosic fractions are reduced. This also assists in biodegradation.

The products of the invention are notably free or hydrated aldehydic groups on C2 and C3 carbons of the basic unit, their intra- and intermolecular hemiacetals, intramolecular C2, C6 hemiacetals, intermolecular C2 and C3 hemialdals, and monoketonic groups on C2 and C3 carbons. Presence of even small amounts of these groups may destabilize main glycosidic bonds and result in formation of irritating products, especially in applications in aqueous systems.

In a final stage of the degradation process after oxidation and isolation of the product during its storage, macromolecular products may be formed which are physiologically ineffective or even have irritating or other negative effects on the organism. In addition we have found that equally undesirable from both the physiological and stability standpoint is the content of bound nitrogen, albeit in small concentrations, mostly occurring in the form of nitrosoether or nitrite groups. These groups may undergo scission leading to formation of nitrogen containing acids which in turn may provoke destruction of the PAGA product during storage.

The invention also provides a pharmaceutical or cosmetic composition incorporating stable microdispersed polyanhydroglucuronic acid and salts thereof of the invention.

The invention will be more clearly understood from the following description thereof given by way of example only.

DETAILED DESCRIPTION OF THE INVENTION

It has been our aim to prepare stable polyanhydroglucuronic acid with controlled physicochemical properties adapted to the intended use, thus reducing or fully suppressing deficiencies of conventional products manufactured as well as broadening the potential scope of applications thereof. This aim is achieved by preparing stabilized microdispersed PAGA with reduced degree of crystallinity, its copolymers with anhydroglucose, and salts thereof, with a high degree of purity.

An important feature of the invention resides in that this microdispersed PAGA, its copolymers with anhydroglucose, and salts thereof, prepared according to the invention, comprising a reduced proportion of the crystalline phase, consists of particles of 0.01 to 1000 $\mu$m in size or fibres with 5 to 30 $\mu$m diameter and up to 30 mm length, with an open surface, containing in their polymeric chain from 8 to 30 per cent by weight of carboxyl groups, at least 80 per cent of these groups being of the uronic type, and a reduced proportion of destabilizing carbonyl groups, in particular aldehydic ones on C2 and C3 carbons of the basic glucopyranosic unit and condensation products thereof, notably intra-and intermolecular 2,6- and 3,6-hemiacetals, 2,3-hemialdals and C2–C3 aldehydes, as well as of bound nitrogen.

Aiming at suppression of the above mentioned deficiencies, especially of low stability, of the PAGA products manufactured thus far, as well as of deficiencies of known methods of preparing the same, is also the method of preparing according to the invention, which yields stable microdispersed PAGA with easily controllable physicochemical characteristics. An important feature of the process consists in that the raw PAGA product obtained by oxidation of a suitable type of natural glucane and cleared, e.g. by washing, of foreign admixtures is transformed, via action of aqueous solutions of salts such as sodium acetate or carbonate or calcium acetate, chloride or carbonate and/or organic or inorganic bases such as alkyl- or alkanolamines or alkali metals or alkaline earth hydroxides, within an oxidative environment constituted by e.g. organic or inorganic peroxides and/or peroxoacids and salts thereof or hypochlorites or chlorites, into an aqueous colloidal dispersion system, simultaneously provoking hydrolysis of original macromolecular chains of PAGA, oxidation of the destabilizing carbonyl groups in the original PAGA to stable carboxyl groups, and hydrolytic removal of bound nitrogen, whereupon the reaction system is coagulated and stabilised by means of a water-miscible coagulating agent, separated microdispersed PAGA or a salt thereof is washed, isolated, and dehydrated using a water-miscible solvent such as C1 to C4 monohydric aliphatic alcohol, or else first modified by some of known physical or chemical methods and then washed, isolated, and dehydrated in much the same way.

EXAMPLES

Example 1

In this example, the raw material for preparing a salt of microdispersed polyanhydroglucuronic acid were cotton linters containing 99.1% b/w (by weight) of $\alpha$-cellulose and oxidised in 60% nitric acid with an admixture of 3.6% nitrous acid at a temperature of 28° C. in analogy with the procedure of GBP 709684. The resulting product contained:

| | |
|---|---|
| carboxyl groups | 13.7% b/w |
| carbonyl groups | 4.2% b/w |
| bound nitrogen | 0.48% b/w |

In a 3000 ml laboratory mixer, 1000 ml of water and 0.158 g of calcium acetate were heated up to 60° C. and stirred at 600 rpm. After dissolution of calcium acetate, 2 g of the above defined oxidised cotton linters containing about 8% of volatile matter were added, temperature increased to 98° C., and the mixture stirred at 2800 rpm for 15 minutes while maintaining the temperature. The temperature was then decreased back to 60° C., pH adjusted to 8.5 by adding sodium hydroxide solution, 25 g of 30% hydrogen peroxide were added, and the hydrolysis continued at the reduced temperature for another 15 minutes. Subsequently the reaction system was cooled down to 40° C., stirring reduced to 300 rpm, and 1500 ml of 92% ethanol were added stepwise during about 10 minutes. The resulting colloid dispersion solution was then filtered, the residue was dispergated into 50% water-ethanol mixture and allowed to stand for one hour. After another filtration the residue was redispergated into 100 ml of isopropanol and allowed to stand for 6 hours. The same procedure was repeated once more, and then the product was filtered and dried in a vacuum drier at a temperature of 40° C.

An analysis of the product obtained yielded:

| | |
|---|---|
| loss on drying | 1.25% b/w |
| carboxyl group content | 16.8% b/w |
| carbonyl groups | 0.5% b/w |
| bound nitrogen content | 0.13% b/w |
| calcium content | 2.1% b/w |
| sodium content | 5.2% b/w |
| particle size | 2 to 5 $\mu$m |
| specific surface area | 98 m$^2$/g |
| Molecular weight | 6 × 10$^4$ Daltons |

The product can be used directly as a hemostatic powder or as a component of an aerosol powder spray.

Example 2

The raw material used was prepared via oxidation of a microbial (1→6)-$\beta$D-gluco-(1→3)-$\beta$D-glucane by gaseous nitrogen oxides, produced in a reaction of dried solid sodium nitrite with 75% b/w nitrous acid, and contained:

| | |
|---|---|
| carboxyl groups | 17.3% b/w |
| carbonyl groups | 1.3% b/w |
| bound nitrogen | 0.44% b/w |

In a 1500 ml laboratory mixer, 500 ml of water and 80 g of the air-dried oxidised raw material were mixed together and stirred at 250 rpm. 12 g of sodium peroxide were added gradually while stirring. The stirrer revolutions were then set at 1800 rpm and the system was maintained at a temperature of 52° C. for 30 minutes. The temperature was then decreased to 35° C., stirrer set at 120 rpm, pH adjusted to 6.0 by adding sodium hydroxide solution, 480 ml of 92% ethanol were added, and the system stirred at 800 rpm for 5 minutes. Subsequently the reaction system containing a colloid dispersion of sodium salt of D-glucurono(1→6)-βD-gluco-(1→3)-βD-glucane was filtered and the residue was dialysed for 4 days against pure water. The dialysed product was redispergated into 500 ml of 80% ethanol and filtered again. The residue was redispergated into 400 ml of isopropanol and allowed to stand for 24 hours. Finally, the product was filtered and dried in a vacuum drier at a temperature of 40° C.

62 g of the product were obtained with the following characteristics:

| | |
|---|---|
| loss on drying | 2.3% b/w |
| carboxyl group content | 18.9% b/w |
| carbonyl groups | 1.1% b/w |
| bound nitrogen content | <0.1% b/w |
| calcium content | 2.1% b/w |
| sodium content | 6.99% b/w |
| particle size | 10 to 20 μm |
| specific surface area | 28 m$^2$/g |
| Molecular weight | Daltons |

The product can be used directly as a hemostatic powder, possibly as an active component of an aerosol formulation, and/or possibly as an active component in cosmetic formulations and the like.

Example 3

Maize starch was processed by oxidation with gaseous nitrogen oxides at a temperature of 15 to 28° C. The intermediate product serving as the raw material in this example contained:

| | |
|---|---|
| carboxyl groups | 23.8% b/w |
| carbonyl groups | 8.2% b/w |
| bound nitrogen | 0.62% b/w |
| volatile matter | 11.1% b/w |

15 g of the above defined oxidised raw material was dispergated by stirring at 600 rpm in 200 ml of water using a 750 ml laboratory mixer. 11 g of sodium hypochlorite were added gradually, pH adjusted to a value of 2.3 by addition of hydrochloric acid, and the hydrolysis was let to occur for 60 minutes at a temperature of 35° C. The pH value was then set at 7.5 by adding sodium hydroxide solution. The stirrer was then set at 2200 rpm and the reaction continued for another 15 minutes. Afterwards, 250 ml of 95% ethanol were added while stirring at 600 rpm for 30 minutes at a temperature of 25° C. The product was then centrifuged, dispergated into 70% ethanol, again centrifuged, redispergated into isopropanol, and allowed to stand for 24 hours. The latter operation was repeated once again, the product filtered and dried in a vacuum drier at 60° C.

An analysis of the product obtained yielded:

| | |
|---|---|
| loss on drying | 3.4% b/w |
| carboxyl group content | 26.9% b/w |
| carbonyl group content | 1.8% b/w |
| bound nitrogen content | 0.18% b/w |
| sodium content | 11.5% b/w |
| particle size | 5–15 μm |
| specific surface area | 75 m$^2$/g |
| Molecular weight | 92,000 Daltons |

The product can be used for analogous purposes as that of Example 2.

Example 4

Medicinal cotton was oxidised in a liquid system involving 3.9% b/w of nitrous acid in 65% nitric acid at temperatures between 3 to 28° C. The intermediate product serving as the raw material in this example contained:

| | |
|---|---|
| carboxyl groups | 24.5% b/w |
| carbonyl groups | 6.9% b/w |
| bound nitrogen | 0.58% b/w |
| volatile matter | 9.9% b/w |

A 1500 ml laboratory mixer was filled with 700 ml of water, and 0.4 g of zinc chloride, 11 g of magnesium nitrate hexahydrate, 35.5 g of calcium chloride, and 32 g of disodiumcarbonate were added gradually under permanent stirring. A white emulsion of the salts was heated to 40° C. while stirring at 150 rpm. Subsequently, 115 g of the oxidised medicinal cotton as described above were added and the stirring continued for another 10 minutes at 40° C. The hydrolysis was then continued with addition of 300 g of 10% solution of peracetic acid for another 10 minutes. The system was agitated at 900 rpm for 30 seconds, cooled down to 20° C., and the fibrillar suspension filtered to remove the liquid. The residue was transferred to a 8000 ml sulfonation flask, suspended in 600 ml of 17% isopropanol/water mixture, and pH value of the system was adjusted to 6.0 by adding 10% solution of calciumdihydroxide in a 8% water solution of saccharose. The suspension was then filtered on a vibrating filter partition, resuspended in 17% isopropanol/water mixture and filtered again. Subsequently, the residue was repeatedly washed with isopropanol and filtered. The residual fibre layer in the form of a nonwoven mat was then dried in a vacuum drier at 50° C.

The procedure yielded 85 g of the product with the following characteristics:

| | |
|---|---|
| loss on drying | 2.6% b/w |
| carboxyl group content | 28.4% b/w |
| carbonyl group content | 0.9% b/w |
| calcium content | 9.5% b/w |
| zinc content | 0.10% b/w |
| magnesium content | 0.41% b/w |
| sodium content | 1.8% b/w |
| bound nitrogen content | 0.11% b/w |

-continued

| | |
|---|---|
| fibre diameter | 10 to 18 $\mu$m |
| fibre length | 5 to 28 mm |
| specific surface area | 29 m$^{2/g}$ |
| Molecular weight | 1.5 × 10$^5$ Daltons |

The product may be used, after appropriate processing, for manufacture of modified wound dressings and similar products with hemostatic effects.

Example 5

Medicinal cotton gauze, alkali-bleached, was oxidised in a liquid system involving 2.8% b/w of nitrous acid in 67% nitric acid at temperatures between 5 to 15° C. The intermediate product serving as the raw material in this example contained:

| | |
|---|---|
| carboxyl groups | 8.4% b/w |
| bound nitrogen | 0.72% b/w |
| volatile matter | 7.5% b/w |

A 5000 ml laboratory mixer was filled with 1500 ml of water, and 300 g of sodium hydroxide were added gradually under permanent cooling and stirring at 120 rpm. After dissolution the temperature was held at 5° C., and 325 g of the oxidised raw material as described above were added under permanent stirring. On completion the stirrer was set at 350 rpm and the temperature maintained at 5 to 8° C. for 15 minutes. The stirrer was slowed down again to 120 rpm, and still while cooling, the value of pH was set at 8.0 by adding hydrochloric acid. The temperature was then increased to 20° C. and 200 g of 30% hydrogen peroxide were added. Subsequently, the system was stirred at 600 rpm for 20 minutes, 1000 ml of concentrated ethanol were added and the stirring continued for another 10 minutes. The product was filtered, redispergated into 1500 ml of 30% ethanol/water mixture, and agitated for 2 hours. The same procedure was then repeated another two times. Finally, the product was redispergated in 1500 ml of methanol, allowed to stand for 6 hours, filtered, and redispergated once more in 1000 ml of isopropanol.

The procedure yielded the product in the form of a microfibrillar suspension with the following characteristics:

| | |
|---|---|
| carboxyl group content | 28.4% b/w |
| carbonyl group content | <0.10% b/w |
| sodium content | 5.9% b/w |
| bound nitrogen content | <0.10% b/w |
| fibre diameter | 10 to 15 $\mu$m |
| fibre length | 1 to 10 mm |
| Molecular weight | 1.5 × 10$^5$ Daltons |

The product can be used, after appropriate processing, for manufacture of modified wound dressings and similar products with hemostatic effects.

An important aspect of the invention consists in the ability of the microdispersed polyanhydroglucuronic acid and salts thereof to form stable dispersions in physiologically indifferent liquids displaying low to zero rate of sedimentation, low viscosity of these colloid-dispersion non-aqueous systems, and no tendency to agglomerate, at concentrations of 0.5 to 15% b/w.

Of important advantage is the fact that the physicochemical properties of the microdispersed polyanhydroglucuronic acid can be controlled to fit the dispergating liquid or mixture of liquids, thus allowing stable systems suitable as spray fillings to be prepared.

Extensive tests have shown that the microdispersed polyanhydroglucuronic acid and salts thereof prepared by controlled hydrolysis and fractionation, mostly in the form of particles smaller than the size of an erythrocyte, is capable of stimulating the activity of histiocytes and macrophages, which represents another essential advantage of the application of such substances. At the same time, they effectively arrest capillary bleeding of the wound area while getting incorporated into the fibrin net formed. Due to small size of the order of microns, the particles of the microdispersed polyanhydroglucuronic acid and salts thereof undergo, dependent on the chemical composition and physiochemical properties, relatively rapid enzymatic hydrolysis in the wound environment yielding glucose and glucuronic acid, substances inherent to living organisms, as final products; in fact, histological observations indicate that they are presumably incorporated into body mucopolysaccharides. Close to neutral pH value of extracts of salts of microdispersed polyanhydroglucuronic acid also substantially contributes to their biocompatibility; no adverse secondary effects due to acidic nature have been reported in their applications.

The presence of reactive carboxyl groups in the microdispersed polyanhydroglucuronic acid and salts thereof is the basis for their ability to chemically bind substances with antibacterial effects such as e.g. derivatives of biguanid, quaternary ammonium salts, or aminosaccharide based antibiotics. Bactericidal activity is also observed for salts or complex salts of certain cations, such as $Zn^{2+}$, $Cu^{2+}$, and to a limited extent $Ag^+$, with microdispersed polyanhydroglucuronic acid.

Similarly, we have observed that preparations based on the microdispersed polyanhydroglucuronic acid and salts thereof display certain insecticidal activity. This activity can be enhanced using hydrophobic reactivity of polyanhydroglucuronic acid molecules which allows to anchor, on the powder substance, non-toxic synthetic derivatives of natural pyrethrins such as pyrethroids, notably Permethrin (cis/trans isomer ratio 1:3). Another advantage of compositions according to the invention is thus represented by the possibility to combine, in a single product, hemostatic, bacteriostatic, and insecticidal function. This is important in veterinary medicine for the treatment of both traumatic and artificial lesions in e.g. sheep and cattle, in that it provides a temporary protection against microbial infection and insect attack during healing.

An example of successful combination of an antibiotic and hemostatic may be represented by the application of neomycine ut sulfas and bacitracinum zincicum bound to a sodium/calcium salt of microdispersed polyanhydroglucuronic acid.

Another problem that had to be solved within the invention concerns the choice of dispergating liquids and propellants to be used in aerosol packaging formulations of the microdispersed polyanhydroglucuronic acid and salts thereof.

Extensive tests have surprisingly revealed that the use of organosols containing several different substituents or highly polar substituents caused the system to easily form coacervates or even to coagulate.

We have found that eg alcoholic dispersions display a relatively low stability with a rapid coagulation and/or sedimentation of particles. The stability is increased with increasing size of the aliphatic chain of the molecule, but the application of higher alcohols is limited from the physiological point of view. We have also found that the hemostatic efficacy of the microdispersed polyanhydroglucuronic acid based products in the initial phase immediately after the spray administration is reduced by the presence of water or polyhydroxycompounds such as glycerol and its derivatives, glycols and polyglycols. Univalent alcohols such as ethanol can induce a stinging pain on application to the wound. Substances of the latter types are therefore preferably avoided in the formulation.

Coagulation and/or sedimentation was surprisingly equally observed in systems where a substance with low polarity has been used, but the molecule contained several different substituents giving rise to an electrostatic non-equilibrium, the Examples of there being dichlorotetrafluoroethane or trichlorofluoromethane. In contrast, low polar substances such as alkanes, C1 to C8 cycloalkanes, or their fluorinated and perfluorinated derivatives, yielded stable dispersion systems with a low sedimentation rate. Examples are methane, ethane, propane, butane, isobutane, pentane, 2-methylbutane, 2-methylpropane, 2,2-dimethylpropane and the like. Substances with 3 to 5 carbon atoms such as pentane, neopentane, or a pure petrol fraction free from mercaptanes and aromatics may preferably be used to reduce loss at administration, to improve fixation of the substance upon the treated area.

We have further found that the organic liquid molecule may also contain a heteroatom, preferably oxygen, in the main chain without deteriorating the system stability. Such substances would involve ethers such as dimethylether, diethylether, but also perfluorinated ethers of the methoxy- or ethoxy-nonafluorobutane type.

Extensive tests have shown that the product, though involving an important number of hydrophilic polar groups, can best be dispergated in low polar or non-polar liquids with a low surface tension and low relative permitivity. In contrast, we have found that liquids with higher polarity and higher surface tension tend to support agglomeration of the product particles and thus to jeopardise the correct function of the aerosol packaging. Besides the effect of microparticles with a large specific surface area, the good dispergability of the microdispersed polyanhydroglucuronic acid and salts thereof may be attributed to their ability to enter, in spite of the presence of hydrophilic groups, hydrophobic interactions with the dispergating liquids. The results indicate that stable dispersion systems can preferably be obtained using those of the above substances which display a value of the relative permitivity (dielectric constant at 25° C. and 10 kHz) less than 10, preferably less than 5, and that of the surface tension less than 30 mN/m, preferably less than 15 mN/m. Thus the substances recommended for use involve, preferably, C3 to C5 alkanes, isoalkanes, or cycloalkanes, 1,1,1,2-tetrafluoroethane, dimethylether, methoxy- and ethoxy-nonafluorobutane and mixtures thereof.

Besides the ability to form low sedimenting dispersion systems, the overall criteria limiting the choice of suitable dispergator/propellant systems further include: physiological indifference (low toxicity, zero or minimum skin and cardiac sensitisation at exposures up to 100000 ppm, no mutagenicity and carcinogenicity, minimum solubility in water and body fluids), indifference in contact with the active substance, high volatility and low heat of evaporation, ability to fix the active substance in the first phase immediately after application on the wound surface, environmental acceptability, and cost.

It is difficult to draw a sharp demarcation line between the dispergating medium suitable for the microdispersed polyanhydroglucuronic acid and salts thereof and the propellant since in some cases both functions can be provided for by one and the same substance such as e.g. n-butane or isobutane. In general, the relevant substances may especially involve:

a) Aliphatic and alicyclic hydrocarbons with 1 to 6 carbon atoms, or aliphatic ethers, notably dimethylether, diethylether, and diisopropylether. While aliphatic hydrocarbons with 1 to 3 carbon atoms could well serve as dispergators for the microdispersed polyanhydroglucuronic acid and salts thereof when under pressure, they evaporate immediately at the output of the spray outlet and thus increase the powder dissipation on spraying and insufficiently fix the powder on the wound surface. It is therefore preferable to use higher hydrocarbons such as n-butane, isobutane, n-pentane, or isopentane for the given purpose. This group may also include petrolether, pentane/isopentane fraction from petroleum distillation, or a mixture of liquid hydrocarbons currently distributed under the name of medicinal petrol, under the obvious condition of being pure enough from aromatic hydrocarbons and mercaptanes. From the ether group, dimethylether can preferably be used with respect to its suitable physicochemical characteristics.

b) Nonflammable compounds known as fluorohydrocarbons (HFC), perfluorocarbons (PFC), and recently introduced hydrofluoroethers (HFE). Compared to chlorofluorocarbons (CFC), the HFC's and PFC's display much reduced life time in the atmosphere and zero to very low ozone-depleting potential (ODP) and global warming potential (GWP). Some may have a slightly increased toxicity and bioreactivity; however, their contact with the wound is very short due to the rapid evaporation rate. The most suitable choice with respect to the properties may be represented by 1,1,1,2-tetrafluoroethane (HFC 134a), or hydrofluoro-ethers such as methoxy-nonafluoroethane (HFE 7100) or 1,1,1,2,3,3-hexafluoro-3-methoxypropane, all of these substances being acceptable from both the physiological and environmental point of view.

Representatives of both above groups are liquids or substances liquefiable at low pressures (0.2–1.4 Mpa) at normal conditions. Further alternatives include:

c) Gaseous substances, which cannot be liquefied at normal conditions, but capable of being absorbed, at least partially, in the powder active substance or in the liquid dispersion system. These include notably carbon dioxide, and nitrous oxide.

d) Gaseous substances not liquefiable at normal conditions and displaying a very limited absorption ability in the liquid dispersion system, such as rare gases, air, and nitrogen.

All of these substances can further be suitably combined with each other to provide for an optimized function of the spray. Based on extensive testing, the preferred combinations include systems such as n-butane or n-pentane/$CO_2$, medicinal petrol/HFC 134a, isopentane/dimethylether, medicinal petrol/HFE 7100/HFC134a, HFE 7100/$CO_2$, n-pentane/HFE 7100/$N_2$.

In summary, the important fact underlying the present invention is that the specifically prepared microdispersed polyanhydroglucuronic acid and salts thereof make it possible to create stable dispersion concentrates in liquids that do not compromise the environment, displaying zero or low values of both the ODP and GWP potentials.

An important advantage of the aerosol packaged hemostatic according to the invention consists in the fact the contents of the packaging can repeatedly be used without the loss of their sterility. The dosing of the active substance can accurately be directed to the wound surface where the powder gets well anchored due to the relatively high speed of incidence of an indifferent dispersion in a liquid that is immiscible with the body fluids and evaporates within a few seconds.

Although certain adverse secondary effects are reported for the above listed dispergating and propellant substances, such as weak narcotic effects or skin degreasing on contact for C5 hydrocarbons, no such effects have been observed during extensive application tests of the sprays according to the invention because of small applied amounts and short contact time.

An additional specific advantage can be attained when using substances listed under a) above or combinations of substances listed under a) and c) above for preparing the stable dispersions of the microdispersed polyanhydroglucuronic acid and salts thereof. Such formulations of the spray allow a simple terminal sterilisation of the finished aerosol packagings to be performed by gamma radiation.

Example 6

A hemostatic composition in pressurised aerosol packaging has been prepared using stable microdispersed polyanhydroglucuronic acid in the form of calcium/sodium salt according to Example 1 above. The equipment used included a stainless steel 1000 liter mixer with a propeller stirrer, a stainless steel 30 liter/min metering pump with inner circulation, and an aerosol filling machine (Pamasol type) with one filling head for the dispersion concentrate and two filling heads for the propellant.

The bulk substance used in this example was a calcium/sodium salt of microdispersed polyanhydroglucuronic acid having the following characteristics:

| | |
|---|---|
| Particle size 20–60 $\mu$m | 2% b/w |
| 10–20 $\mu$m | 32% b/w |
| $\leq$10 $\mu$m | 66% b/w |
| specific surface area | 105 $m^{2/g}$ |
| Carboxyl group content (total) | 20.2% b/w |
| carboxyl group content (uronic) | 18.2% b/w |
| free formaldehyde | 0% b/w |
| foreign particles | 0% b/w |
| calcium content | 3.9% b/w |
| sodium content | 5.6% b/w |
| bound nitrogen content | 0.02% b/w |

Chlorohexidine hydrochloride (Ferrosan) in concentration of 0.1% b/w was added as a bacteriostatic adjuvant. The dispergation/propellant system involved a liquid hydrocarbon mixture (known as medicinal petrol) with density of 652 $kg/m^3$, boiling point 55° C., and residue after evaporation <2 ppm, and 1,1,1,2-tetrafluoroethane (HFC 134a).

40 kg of the active substance was placed into the mixer, 150 liters of the liquid hydrocarbon mixture added, and the system stirred at 600 rpm for 5 minutes. After addition of 1 kg of chlorohexidine hydrochloride and of another 250 liters of the liquid hydrocarbon mixture, the system was further stirred until a uniform dispersion was obtained. The metering pump was used to dose the dispersion via the filling head of the filling machine into aerosol cans of 80 ml nominal volume in doses of 31 g per can. After inserting a suitable valve, another filling head was used to add 18 g per can of the 1,1,1,2-tetrafluoroethane propellant. The finished spray can be used for treatment of bleeding wounds by both the professional or a layman.

Example 7

The same equipment was used as in Example 6. The active substance consisted of two components, MDOC1 with the same characteristics as in Example 6, and MDOC2 involving a zinc/calcium/sodium salt of microdispersed polyanhydroglucuronic acid having the following properties:

| | |
|---|---|
| carboxyl group content | 19.5% b/w |
| free formaldehyde | 0% b/w |
| zinc content | 9.5% b/w |
| calcium content | 3.9% b/w |
| sodium content | 5.6% b/w |
| bound nitrogen content | 0% b/w |

Neomycinum ut sulfas and Bacitracinum zincicum were used as antibacterial adjuvants, n-pentane having density of 625 $kg/m^3$, and boiling point 36° C., as the dispergator, and carbon dioxide (edible grade quality) as the propellant. 38.8 kg of MDOC1 and 1.2 kg of MDOC2 was placed into the mixer together with 0.132 kg of Neomycinum ut sulfas and 0.143 kg ($10^7$ IU) of Bacitracinum zincicum, 200 liters of n-pentane added, and the system thoroughly stirred. Another 200 liters of n-pentane were then added and stirred for another 10 minutes. Aerosol cans of 80 ml nominal volume were then filled in doses of 31 g per can, and, after inserting the valves, another filling head was used to pressurise the can by addition of 2 g of compressed carbon dioxide.

The finished spray can be used for professional treatment of bleeding wounds and lesions.

Example 8

A thoroughly homogenised uniform powder mixture of microdispersed polyanhydroglucuronic acid in the form of magnesium/calcium/sodium and zinc/calcium/sodium salts in the mass ratio of 32:1 is filled into aerosol cans of 210 ml nominal volume in doses of 8 g per can on a powder dosing machine (Bosch). Upon closing the can with an appropriate valve, the can is pressurised on the aerosol filling machine by adding 20 g of n-butane and 30 g of dimethylether. Finished and gamma sterilised sprays then can be used for treatment of smaller burns or scalds. It can also, be applied in e.g. urological or gynecological surgery.

Example 9

Into the mixer as described in Example 6, 25 kg of calcium/sodium salt of microdispersed polyanhydroglucuronic acid (Example 6), 5.0 kg of calcium stearate, 0.4 kg of chlorohexidine hydrochloride, and 7.7 kg of Permethrin with cis/trans ratio of 25:75 (ICI Plant Protection) are successively placed. After addition of 400 liters of n-pentane and 99 kg of methoxy-nonafluorobutane (HFE 7100), the contents of the mixer are stirred for 15 minutes. The uniform dispersion is then filled into aerosol cans of 210 ml nominal volume in doses of 110 g per can on the filling machine and closed with an appropriate valve. Another filling head is then used to add 50 g per can of dimethylether.

The finished spray is designed for use in veterinary practice for treatment of wounds and lesions in e.g. sheep and cattle, simultaneously providing a temporary protection against microbial and/or insect attack.

Example 10

A hydrophilised adduct (MDOC-ACV) of 9-[(2-hydroxymethoxy)-methyl]-guanin (acyclovir) and a calcium/sodium salt of microdispersed polyanhydroglucuronic acid (Example 6) was prepared according to Example 1 above by a hydrolytic treatment with controlled pH and fractionation, the content of acyclovir in the MDOC-ACV adduct being 50.5% b/w.

A homogenised mixture of the adduct, the magnesium/calcium/sodium salt of microdispersed polyanhydroglucuronic acid according to Example 6, and the zinc/calcium/sodium salt thereof according to Example 7 in the mass ratio of 8.7:0.3:1.0 is filled into aerosol cans of 120 ml nominal volume in doses of 4 g per can on a powder dosing machine (Bosch). Upon closing the can with an appropriate valve, the aerosol filling machine is used to pressurise the can by adding 25 g of 2,2-dimethylpropane (neopentane) with a density of 625 kg/$m^3$, and boiling point 9.6° C., on filling head 1, and 23 g of dimethylether with a density of 668 kg/$m^3$.

The finished spray is packed and sterilised by gamma radiation with a dose of 25 kGy and used as a dusting powder in the treatment of e.g. herpes zoster, enabling an easy application and good efficacy even in hairy areas of the body.

The invention is not limited to the embodiments hereinbefore described which may be varied in detail.

What is claimed is:

1. A stable microdispersed polyanhydroglucuronic acid or salt thereof containing, in its polymeric chain, from 8 to 30 per cent by weight of carboxy groups, at least 80 per cent by weight of which are in uronic group form, at most 5 per cent by weight of carbonyl groups, and at most 0.5 per cent by weight of bound nitrogen, and being either in particle form having a size of from 0.1 to 1000 μm or in fiber form having a diameter of from 5 to 30 μm and a length of up to 30 mm.

2. The polyanhydroglucuronic acid or salt thereof as claimed in claim 1 containing in its polymeric chain at most 0.2 per cent by weight of bound nitrogen.

3. The polyanhydroglucuronic acid or salt thereof as claimed in claim 1 wherein the molecular mass of the polymeric chain is from $1\times10^3$ to $3\times10^5$ Daltons.

4. The polyanhydroglucuronic acid or salt thereof according to claim 3 wherein the molecular mass of the polymeric chain ranges from $5\times10^3$ to $1.5\times10^5$ Daltons.

5. The polyanhydroglucuronic acid or salt thereof as claimed in claim 1 wherein the content of carboxyl groups is in the range of from 12 to 26 per cent by weight, at least 95 per cent of which are uronic groups.

6. The polyanhydroglucuronic acid or salt thereof as claimed in claim 1 containing at most 1 per cent by weight of carbonyl groups.

7. The polyanhydroglucuronic acid or salt thereof according to claim 1 wherein the carbonyl groups are selected from the group consisting of intra- and intermolecular 2,6- and 3,6-hemiacetals, 2,4-hemialdals and C2–C3 aldehydes.

8. The stable microdispersed polyanhydroglucuronic acid or salt thereof according to claim 1, where the polyanhydroglucuronic acid or salt is in particle form having a size of from 0.1 to 1000 μm.

9. The stable microdispersed polyanhydroglucuronic acid or salt thereof according to claim 1 made up of fibers of from 5 to 30 μm in diameter and up to 30 mm in length.

10. A pharmaceutical or cosmetic composition incorporating stable microdispersed polyanhydroglucuronic acid or salt thereof as claimed in claim 1.

11. A composition as claimed in claim 10 in the form of a haemostatically active aerosol composition.

* * * * *